United States Patent [19]

Boen et al.

[11] Patent Number: 5,374,738
[45] Date of Patent: Dec. 20, 1994

[54] SYNTHESIS OF 1,2-BENZISOTHIAZOLE-1,1-DIOXIDES

[75] Inventors: Laurence Boen, Wayne, N.J.; David J. Batal, Chicago, Ill.; Stephen A. Madison, New City, N.Y.

[73] Assignee: Lever Brothers Company, Division of Conopco, Inc., New York, N.Y.

[21] Appl. No.: 156,173

[22] Filed: Nov. 22, 1993

[51] Int. Cl.$^5$ .................................... C07D 275/06
[52] U.S. Cl. .................................... 548/207
[58] Field of Search .................................... 548/207

[56] References Cited

U.S. PATENT DOCUMENTS

| | | | |
|---|---|---|---|
| 4,181,660 | 1/1980 | Borror et al. | 548/110 |
| 5,041,232 | 8/1991 | Batal et al. | 252/94 |
| 5,210,196 | 5/1993 | von Oppolzer | 548/207 |

OTHER PUBLICATIONS

Abramovitch et al., J. Org. Chem., vol. 43 No. 6 (1978) pp. 1218–1226.
Ann. Chim. (Rome) 61, (6), pp. 399–413 (1971).
J. Chem. Soc. Perkin 1, pp. 3,006–2,010 (1972).
J. Chem. Soc. Perkin 1, pp. 2,589–2,594 (1974).
J. Org. Chem. 57, pp. 5,328–5,334 (1992).

*Primary Examiner*—Joseph Paul Brust
*Assistant Examiner*—Mary Susan H. Gabilan
*Attorney, Agent, or Firm*—Milton L. Honig

[57] ABSTRACT

A process is provided for preparing 1,2-benzisothiazole-1,1-dioxides having structure (1):

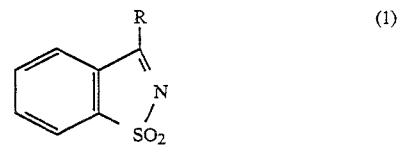

where R is a $C_1$–$C_{20}$ alkyl or aryl radical, the process comprising the steps of:
(a) preparing a solution in an anhydrous solvent of a saccharin salt having structure (2):

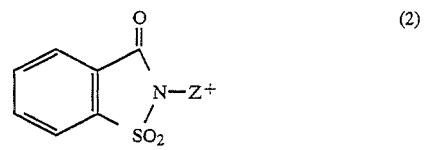

where $Z^+$ is a metallic cation other than magnesium; and
(b) reacting heterogeneously the saccharin salt with an organomagnesium reagent in a relative magnesium to saccharin salt molar ratio of 1:1.

6 Claims, No Drawings

SYNTHESIS OF 1,2-BENZISOTHIAZOLE-1,1-DIOXIDES

BACKGROUND OF THE INVENTION

1. Field Of the Invention

The invention relates to an improved process for preparation 1,2-benzisothiazole-1,1-dioxides, especially 3-methyl substituted derivatives.

2. The Related Art

Sulfonimines such as 1,2-benzisothiazole-1,1-dioxides have recently been disclosed as bleach catalysts for cleaning fabrics. See U.S. Pat. No. 5,041,232 (Batal et. al.) which discloses 3-methyl-1,2-benzisothiazole-1,1-dioxide Known as SULF-11. The unusually active nature of SULF-11 has focused attention on improved synthetic routes to this material.

Pseudosaccharin chloride in combination with a malonate ester have been reacted to provide the basis for one type of route to these sulfonimides. See articles by Melchiorre, Giannella and Gualtieri, *Ann. Chim. (Rome)* 61 (6), p. 399 (1971) and Carrington, Clark, Ewes and Scrowston, *J. Chem. Soc., Perkin* 1, p. 3006 (1972).

A second reported route has involved the reaction of saccharin with two molar equivalents of a Grignard or organolithium salt. This route is described in Abramovitch, Smith, Humber, Purtschert, Srinivasan and Singer, *J. Chem. Soc., Perkin* 1, p. 2589 (1974) and Hermann, Campbell, Greenwood, Lewis and Wolfe, *J. Org. Chem.*, 57, p. 5328 (1992).

Common to all the references is the underlying assumption that it is necessary to employ a soluble saccharin reactant. Apparently the art as avoided insoluble saccharin reactants that would require a heterogeneous reaction scheme.

Of particular disadvantage in the known art is the use of two moles organometallic reagent. Since organometallic reagents are quite expensive and often pyrophoric, it would be advantageous to limit amounts or these reagents. Furthermore, Grignard reagents of the known art require considerable volumes of solvent. Environmental, cost, safety and other reasons encourage limitation of the solvent volumes.

Accordingly, it is an object of the present invention to provide an improved synthesis of 1,2-benzisothiazole-1,1-dioxides which limits the amount of organometallic reagent necessary for the reaction.

A further object of the present invention is to provide an improved synthesis of 1,2-benzisothiazole-1,1-dioxides which limits the volume of solvent necessary in the reaction.

These and other objects of the present invention will become apparent through the following summary, detailed discussion and examples.

SUMMARY OF THE INVENTION

A process is described for preparing 1,2-benzisothiazole-1,1-dioxides having structure (1):

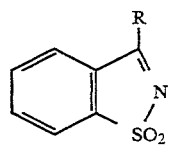

where R is a $C_1$–$C_{20}$ alkyl or aryl radical, the process including the steps of:

(a) preparing a solution in an anhydrous solvent of a saccharin salt having structure (2):

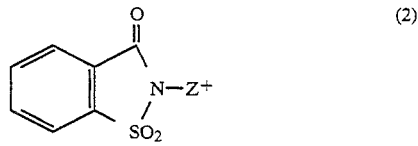

where $Z^+$ is a metallic cation other than magnesium; and (b) reacting the saccharin salt with an organomagnesium reagent in a relative magnesium to saccharin salt molar ratio of about 1:1.

DETAILED DESCRIPTION

Now it has been discovered that compounds having structure (1):

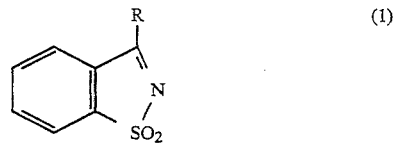

where R is a $C_1$–$C_{20}$ alkyl or aryl radical, preferably methyl, ethyl, propyl, butyl, octyl or phenyl, can be synthesized from an ether insoluble mixed metal magnesium saccharin salt intermediate. Only a single mole of Grignard reagent per mole of saccharin salt reagent is necessary. Solvent levels in this reaction can also be kept to relatively low levels.

Essential to the invention is the use of a saccharin salt having structure (2):

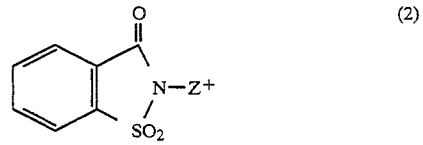

where $Z^+$ is a metallic cation, preferably an alkali metal such as sodium or potassium cation. Useful but less preferred metallic cations can be selected from elements under Groups IA, IIA–VIIA and IB–IVB of the Periodic Table. Examples include calcium, barium, titanium, zinc, aluminum, tin and lead.

Structure (2) can be formed in situ from saccharin and a base such as sodium $C_1$–$C_{10}$ alkoxide (e.g., sodium methylate) or sodium hydroxide;.

Once structure (2) has been prepared, the second step of the process involves reaction with a magnesium Grignard reactant of the formula RMgX. where X is a halide such as chloride or bromide. The relative molar ratio of structure (2) to magnesium Grignard reactant will be about 1:1.

Solvents suitable for the reaction should be anhydrous. As with all Grignard reactions, water will decompose the magnesium Grignard before reaction with the saccharin salt. Suitable solvents include $C_4$–$C_{20}$ ethers and saturated $C_5$–$C_{20}$ hydrocarbons. Particularly preferred is tetrahydrofuran. Solvent amount can be limited to no higher than an amount necessary to form at least a 1.8 molar product (structure 1) solution. Of course, in those instances such as small scale reactions where solvent disposal is of little consequence, any level of solvent would be suitable.

An intermediate magnesium salt of structure (3):

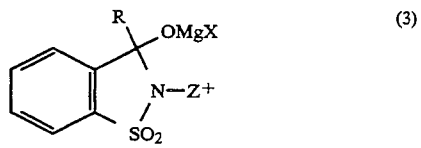

or solvated form, in which an equivalent molar amount of solvent complexes with the magnesium atom, results from the reaction.

Illustrative of the solvated form is structure (4):

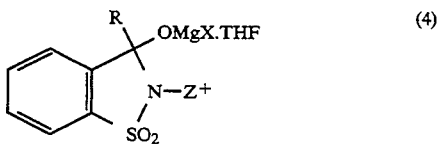

Intermediate structures (3) and (4) can be isolated, transported to another vessel or reacted in situ with water to form structure (1).

The following examples will more fully illustrate embodiments of this invention. All parts, percentages and proportions referred to herein and in the appended claims are by weight unless noted otherwise.

EXAMPLE 1

Preparation of Sodium Saccharin

A three-neck 100 ml round bottom flask was fitted with overhead stirrer, condenser and inlet/outlet for nitrogen atmosphere. The flask was charged with 7.32g saccharin (0.04 mole) and 2.16g (0.04 mole) anhydrous sodium methylate in 50 ml anhydrous methanol. The mixture was stirred ana heated to reflux for about 10–20 minutes under nitrogen. Most of the solids went into solution. The system was then set-up for distillation. Methanol was removed under reduced pressure. Colorless solids of sodium saccharin remained in the flask.

Reaction Of Sodium Saccharin with Methyl Magnesium Chloride

About 30 ml anhydrous tetrahydrofuran was added to the sodium, saccharin solids prepared above. Thereto was dropwise added 13 ml of a 3.0 molar methyl magnesium chloride solution in THF (0.04 mole of active Grignard). An ice-bath was maintained around the flask for cooling. The reaction mixture remained heterogeneous throughout the addition of the methyl magnesium chloride. After addition, the reaction mixture was stirred at room temperature over night.

Thereafter the reaction mixture was separated by first removing tetrahydrofuran on a rotary evaporator. The solids remaining were treated with water and concentrated hydrochloric acid to pH of about 1.0. Solids obtained were filtered, washed with water and suction-dried. Obtained were 7.33g of 3-methyl-1,2-benzisothiazole-1,1-dioxide. FT-NMR(CDCl$_3$)δ2.7(S,3) and 7.6–8.0(m,4).

EXAMPLE 2

Several experiments were conducted to evaluate the advantages of the Grignard reagent reaction with sodium saccharin (present invention) and that with saccharin, (Abramovitch et. al., *J. Chem. Soc. Perkin 1*, 2589 (1974)), to determine advantages of the present synthetic route.

Two important differences were noted in the physical and chemical properties of the magnesium salt intermediates derived from these processes.

(1) Significant reductions in the use of THF solvent in the Grignard reagent reaction of saccharin caused the reaction mixture to undergo physical and chemical change to a hard cake (substance). Mechanical stirring problems resulted which eventually caused complete stoppage of stirring. The same reaction of Grignard reagent with sodium saccharin at similar reductions of THF solvent provided free flowing reaction mixtures with no hard caking and stirring problems.

(2) The Grignard reagent reaction of saccharin at sufficient amounts of THF solvent did prevent hard caking but resulted in the formation of magnesium salt intermediate solids which were chemically bound to the THF solvent in the form of a solid gel. This solid gel was not filterable by way of simple filtration to remove THF solvent in washing off any unreacted Grignard reagent. The same Grignard reagent reaction of sodium saccharin, by contrast, provided free-flowing magnesium salt intermediate solids. These were easily retrievable by way of simple filtration to remove THF solvent and washing off any unreacted Grignard reagent, and further drying.

These differences in physical/chemical properties of the respective Na/Mg and di-Mg salt solids are best appreciated by reviewing the time required for THF removal during product work-up. The table outlines these results.

| Mg Salt Interm. from | THF Removal Method | Estimated Time |
|---|---|---|
| Saccharin | Vacuum distillation | 30–45 mins. |
| Na-Saccharin | Vacuum filtration | 1–3 mins. |

Note:
Times based on 0.04 mole runs of (Na) saccharin using a total 58 ml THF solvent.

The foregoing description and examples illustrate selected embodiments of the present invention. In light thereof, various modifications will be suggested to those skilled in the art all of which are within the purview of the invention.

What is claimed is:

1. A process for preparing 1,2-benzisothiazole-1,1-dioxides having structure (1):

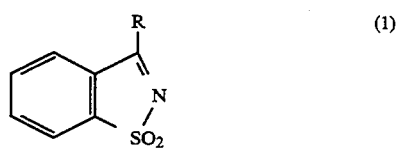

where R is a $C_1$–$C_{20}$ alkyl or aryl radical, the process comprising the steps of:

(a) preparing a solution in an anhydrous solvent of a saccharin salt having structure (2):

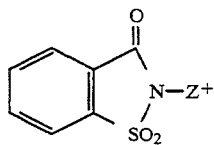

(2)

wherein Z+ is a metallic cation other than magnesium:

(b) reacting heterogeneously the saccharin salt with an organomagnesium Grignard reagent in a relative Grignard reagent to saccharin salt molar ratio of 1:1 to form an intermediate magnesium salt of structure (3):

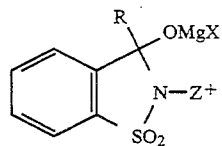

(3)

or solvated form, in which an equivalent molar amount of solvent complexes with the magnesium atom and wherein X is a halide; and (c) hydrolyzing with water the intermediate magnesium salt.

2. A process according to claim 1 wherein the solvent is selected from the group consisting of $C_4$–$C_{20}$ ethers and $C_5$–$C_{20}$ hydrocarbons.

3. A process according to claim 2 wherein the ether is tetrahydrofuran.

4. A process according to claim 3 wherein the solvent is present in an amount no higher than necessary to form at least 1.8 mole of structure (1).

5. A process according to claim 1 wherein the metallic cation is selected from the group consisting of sodium and potassium cations.

6. A process according to claim 1 wherein R is methyl.

* * * * *